United States Patent
Bitzer et al.

(10) Patent No.: US 10,524,673 B2
(45) Date of Patent: Jan. 7, 2020

(54) IMPLANTABLE PRESSURE SENSOR

(71) Applicant: BIOTRONIK SE & Co. KG, Berlin (DE)

(72) Inventors: Andreas Bitzer, Zurich (CH); Alois Pfenniger, Biel (CH); Henning Ebert, Berlin (DE); Andre van Ooyen, Berlin (DE); Joachim Elsner, Berlin (DE)

(73) Assignee: BIOTRONIK SE & Co. KG (DE)

( * ) Notice: Subject to any disclaimer, the term of this patent is extended or adjusted under 35 U.S.C. 154(b) by 398 days.

(21) Appl. No.: 15/262,743

(22) Filed: Sep. 12, 2016

(65) Prior Publication Data

US 2017/0095163 A1    Apr. 6, 2017

(30) Foreign Application Priority Data

Oct. 1, 2015 (DE) ........................ 10 2015 116 648

(51) Int. Cl.
*A61B 5/0215* (2006.01)

(52) U.S. Cl.
CPC ...... *A61B 5/0215* (2013.01); *A61B 2562/028* (2013.01); *A61B 2562/0247* (2013.01); *A61B 2562/168* (2013.01)

(58) Field of Classification Search
CPC ............ A61B 5/0215; A61B 2562/168; A61B 2562/0247
See application file for complete search history.

(56) References Cited

U.S. PATENT DOCUMENTS

| | | | |
|---|---|---|---|
| 4,576,181 A * | 3/1986 | Wallace | A61B 5/0215 600/488 |
| 4,593,703 A | 6/1986 | Cosman | |
| 6,221,024 B1 * | 4/2001 | Miesel | A61B 5/0215 600/486 |
| 7,591,185 B1 | 9/2009 | Mothilal et al. | |
| 8,127,618 B1 * | 3/2012 | Zhao | A61B 5/0215 607/119 |
| 8,142,362 B2 | 3/2012 | Keilman et al. | |
| 8,573,062 B2 | 11/2013 | Zhao et al. | |
| 2010/0018494 A1 * | 1/2010 | Obermeier | G01L 9/0042 123/198 R |
| 2012/0130219 A1 * | 5/2012 | Zhao | A61B 5/0215 600/373 |
| 2014/0155710 A1 | 6/2014 | Rowland et al. | |
| 2016/0029956 A1 | 2/2016 | Rowland et al. | |
| 2016/0249818 A1 | 9/2016 | Philipp et al. | |
| 2016/0324443 A1 | 11/2016 | Rowland et al. | |

FOREIGN PATENT DOCUMENTS

| | | | | |
|---|---|---|---|---|
| DE | 102011054732 A | 4/2013 | | |
| DE | 102011054732 A1 * | 4/2013 | ........... | G01L 19/141 |
| WO | WO 2013/003754 A1 | 1/2013 | | |
| WO | WO 2014/197101 A2 | 12/2014 | | |

OTHER PUBLICATIONS

European Search Report, 16188459.8-1657, dated Feb. 27, 2017.

* cited by examiner

*Primary Examiner* — Meredith Weare
(74) *Attorney, Agent, or Firm* — Craig A. Fieschko, Esq.; DeWitt LLP (57) ABSTRACT

The invention describes an implantable pressure sensor having a housing, wherein the housing has walls and two or more pressure transfer membranes bounding an internal volume, wherein the pressure transfer membranes are not coplanar.

19 Claims, 11 Drawing Sheets

FIG. 6a

IMPLANTABLE PRESSURE SENSOR

FIELD OF THE INVENTION

The invention relates to an implantable pressure sensor, in particular a miniature pressure sensor, which can be implanted into an animal or human body.

BACKGROUND OF THE INVENTION

Pressure sensors including microelectromechanical systems (MEMS) and associated chip systems are known; for example, such pressure sensors are used in therapeutic implants in order to improve the heart function of a patient. Chip systems used for such purposes must on the one hand deliver sufficiently precise measurement results, and on the other hand must have very small dimensions so that they can be implanted without difficulty and do not limit the physiological activity of the organism, for example, when used for blood pressure measurements in the pulmonary artery.

A MEMS chip must generally be protected if it is to be used in a reactive medium, for example in blood. Such protection is often provided by embedding it in an incompressible and inert liquid, and hermetically sealing it in a housing with respect to the reactive medium. The liquid (for example oil) here serves as a pressure transfer medium so that the external pressure can be conducted via the housing (often via a thin membrane on the housing), through the liquid, and to the MEMS chip. Titanium, for example, is suitable as a housing material on account of its long-term stability and high biocompatibility.

In the patient's blood, temperature changes of a few degrees Celsius can usually occur, thus resulting in volume and pressure changes of the pressure transfer medium within the housing. The chip also experiences temperature changes during sterilization, for example by means of ethylene oxide, wherein temperature differences of approximately 30 degrees Celsius occur. Such temperature (and thus volume and pressure) increases can damage the housing's membrane or the MEMS chip where a conventional pressure sensor housing is provided. The housing usually has a low flexibility or elasticity due to the material properties of the housing and the relatively high thickness of the housing walls in comparison to the overall size of the housing, and thus the pressure transfer medium's volume changes lead to high pressure changes within the housing. As a result, the measured pressure values of the MEMS chip are distorted because the pressure values to be measured are superimposed with temperature-induced pressure fluctuations inside the housing.

U.S. Pat. No. 8,573,062 describes the use of a pressure transfer membrane for a MEMS chip sensor, with the membrane covering a window which is formed in the side wall of the housing of the sensor. U.S. Pat. No. 8,142,362 describes a pressure transfer membrane situated on the end face of the housing.

Previous solutions for reducing the temperature dependence of MEMS chip sensor systems cannot reduce the distortions in measured pressure values to negligible levels compared with the pressure values to be measured in the body. Further problems include relatively high manufacturing expense and the housings limited ability to withstand material stresses and forces arising from volume changes of the pressure transfer medium. Joints created in the housing during manufacturing can be torn open by tensile stresses when the internal volume of the housing expands.

SUMMARY OF THE INVENTION

The invention seeks to provide an implantable pressure sensor with improved insensitivity to temperature changes in the operating environment, and greater resistance to the accompanying material stresses. A preferred version of the invention involves an implantable pressure sensor having a housing, with the housing including outer walls and an inner volume. The housing has at least two pressure transfer membranes, wherein the surfaces of the membranes are not situated in a common plane. The use of such pressure transfer membranes provides multiple discontiguous housing surfaces having greater flexibility or elasticity, thereby reducing the pressure inside the housing in the event of temperature fluctuations. Because the pressure transfer membranes are not coplanar, the stresses/forces on the housing created by interior volume changes can also at least partially balance each other out, thereby increasing the robustness of the housing.

In a preferred version of the invention, the pressure transfer membranes each form part of at least two different outer walls of the housing, preferably outer walls arranged opposite one another. The housing is preferably formed at least in part as a cuboid, cylinder, sphere or ellipsoid, though other forms (e.g., having polygonal or circular elliptical cross-sections) can be used. Since the pressure membranes are situated on opposite housing walls, forces and stresses over the housing are more uniformly distributed in the event of volume changes inside the housing. This consequently provides lower stress maxima, reducing the risk of plastic (permanent) deformation or failure at sensitive regions of the housing and providing greater robustness in response to temperature fluctuations. A particularly preferred arrangement is to provide the housing with planar minor-symmetrical surfaces, with a preferred example being a housing configured as a flat cuboid wherein planar rectangular pressure transfer membranes are arranged opposite one another on two outer walls. The pressure transfer membranes can be provided in corresponding windows formed in the housing, as by having them cover the windows and fixing them to the housing at their edges, or clamping them in the windows.

In the foregoing or alternative versions of the invention, at least one outer wall of the housing has a reversibly deformable region. With reversibly deformable regions of the outer wall, the flexibility or elasticity of the housing is increased, since such a region compensates for stresses and threes created by volume changes within the housing. The reversibly deformable region(s) therefore does not transfer the stresses/forces to the regions of the housing that are less elastic. For example, a reversibly deformable region of this type can be used in the zone between the elastic pressure transfer membrane and outer wall areas of the housing that are less elastic, such that these zones provide relief when stress is applied.

Particularly advantageous properties for the housing are achieved when the pressure transfer membranes are coupled to the housing via a reversibly deformable region of an outer wall.

The housing preferably has at least one recess, wherein the recess is configured to accommodate deformations of the inner volume and/or of at least one pressure transfer membrane and/or of at least one outer wall caused by thermal expansion effects. The recess is preferably situated in the inner volume of the housing, and can be formed (for example) as an aperture (e.g., a hole, gap, or through-slot), or a depression (e.g., a slot, notch, groove or incision) which preferably defines a flexible deformable region.

The recess is preferably arranged between the MEMS chip and the housing, such that it at least partially prevents the direct contact of the MEMS chip and the housing, whereby the MEMS chip is better protected against influences distorting the pressure measurements. The recess is preferably situated in areas in which greater deformations are anticipated due to thermal expansion effects of the pressure sensor, for example at areas bordering any reversibly deformable region(s) of the outer wall of the housing.

The deformable region of an outer wall can also be generated by suitable placement of the recess, for example by placement of a through-slot along a region of the outer wall so that this region can freely deform and return in the event of temperature changes. The reversibly deformable region of an outer wall can also be generated by reducing the thickness of the outer wall at suitable points by removal of wall material.

Preferably, at least one pressure transfer membrane borders the recess, or is coupled thereto. It is also (or alternatively) preferred that at least one outer wall borders the recess, or is coupled thereto.

By use of housing walls with high elasticity, and/or by spacing the MEMS chip from the housing with one or more recesses, the pressure sensor compensates for pressures created inside the housing by thermal expansion, and for other stresses and forces that act on the housing. The invention encompasses various arrangements and variations of these housing elements, which can be fabricated from different materials suitable for the application at hand.

The housing of the invention can include a support module situated within the internal volume of the housing, wherein the recess at least partially bounds the support module. The support module is preferably coupled to at least one outer housing wall, and a MEMS pressure sensor chip is connected to the support module within the internal volume of the housing. The support module supports the MEMS chip, and owing to the recess, the regions of direct material connection between the support module and the rest of the housing (in particular the outer walls of the housing) are reduced. The MEMS chip supported on the support surface is likewise decoupled at least in part from the rest of the housing by the recess. For example, the MEMS chip may be supported in the housing by a support module configured as a rib (which is at least partially bounded by a recess), with the support module and MEMS chip thereby having reduced contact with the rest of the housing.

The internal volume of the housing can preferably be filled with a pressure transfer medium, such as oil. The outer walls of the housing may include one or more apertures extending to the internal volume of the housing. Such an aperture may define a via for contacting the MEMS chip with other electronic components, such as a battery or an antenna. An aperture can also constitute a passage through which the interior of the housing can be filled with the pressure transfer medium. The aperture can be selectively closed.

The housing is preferably at least partially fabricated from titanium, though other or additional materials may be used. The thickness of the pressure transfer membrane is preferably no more than 30 μm, and more preferably no more than 10 μm. This provides sufficient flexibility, and at the same time stability, for the housing of the pressure sensor. The housing is preferably configured so that measurement accuracies of approximately 2 mbar can be attained with the MEMS chip.

BRIEF DESCRIPTION OF THE DRAWINGS

In the drawings, like elements are designated by like reference numerals. The drawings are merely schematic illustrations of exemplary versions of the invention, and the invention should not be regarded as being limited to these examples.

DETAILED DESCRIPTION OF EXEMPLARY VERSIONS OF THE INVENTION

Figure 1:
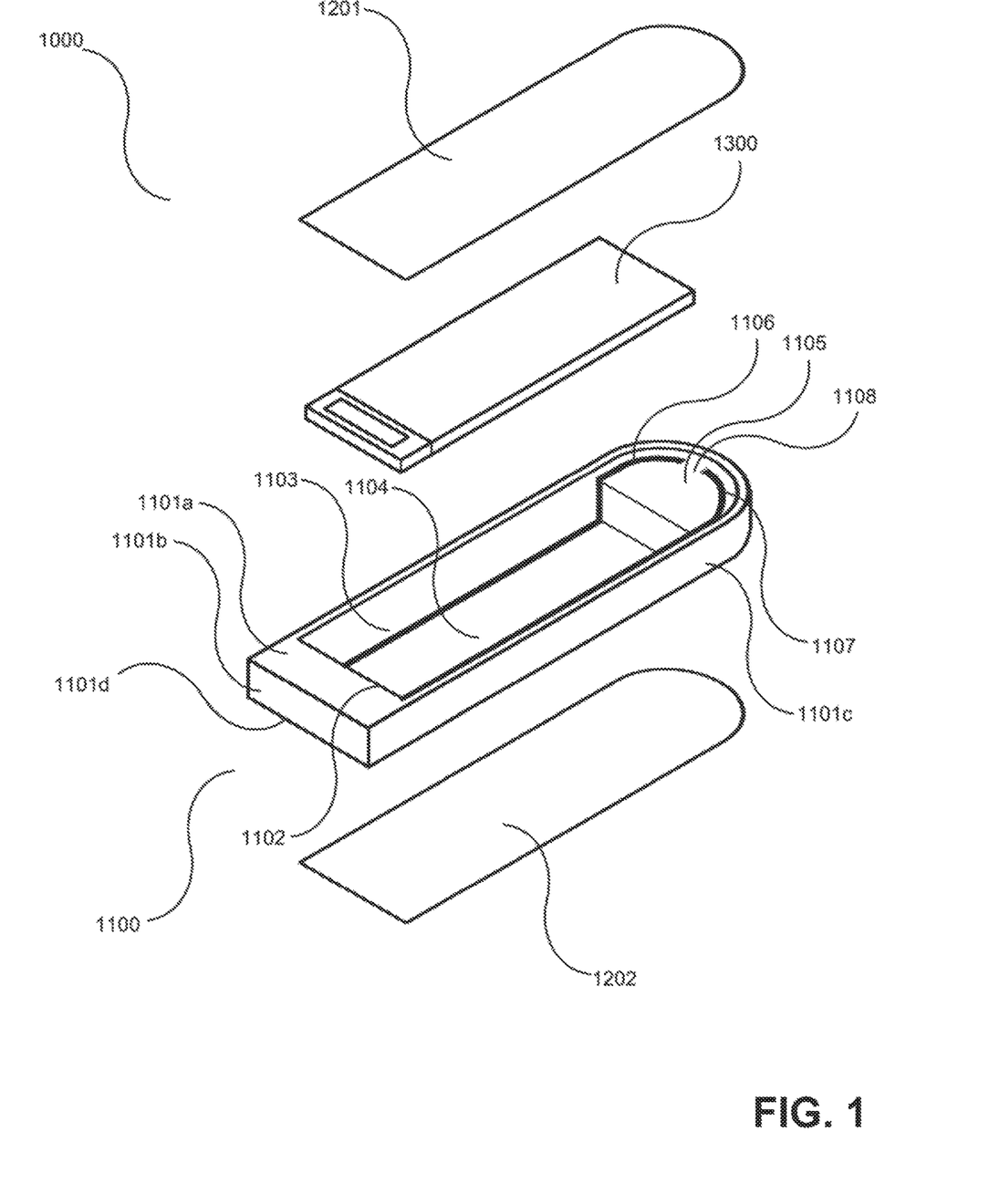
FIG. 1 shows an exploded view of an exemplary version of an implantable pressure sensor.
Figure 1A:
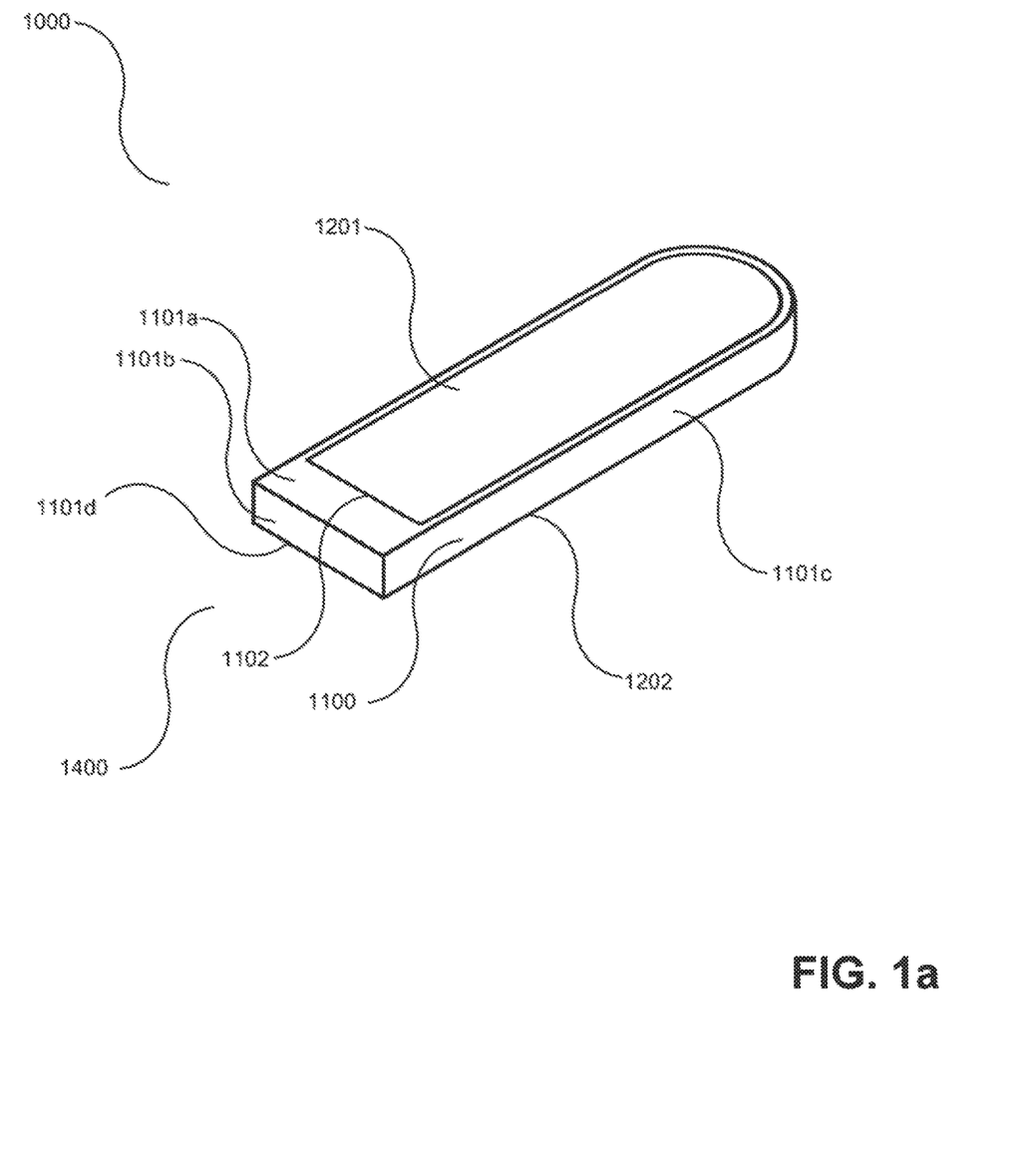
FIG. 1a shows a perspective view of the implantable pressure sensor of FIG. 1 in a finished/assembled form.
Figure 1B:
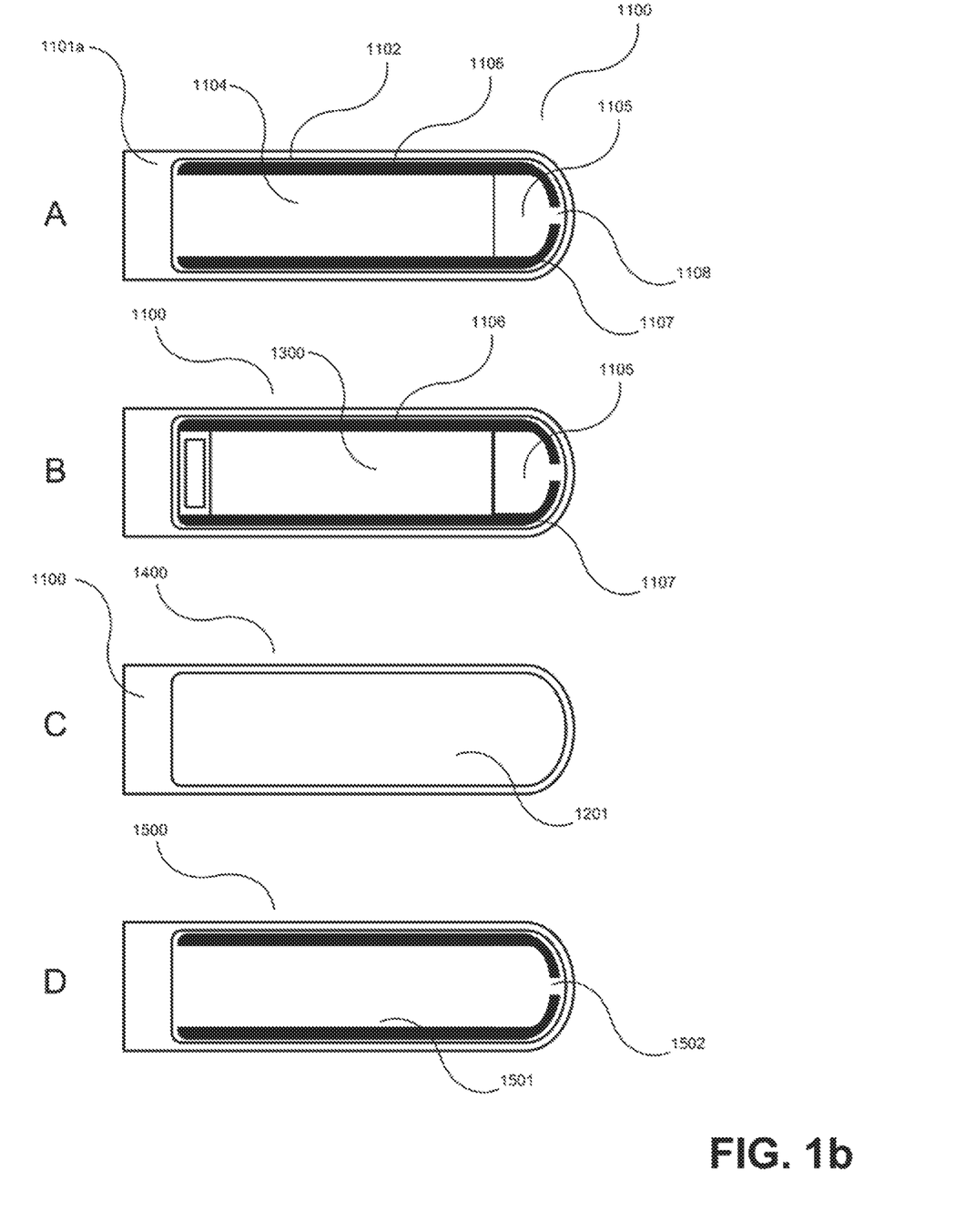
FIG. 1b shows plan views of the implantable pressure sensor of FIG. 1.

FIGS. 1, 1a and 1b show an exemplary version of an implantable pressure sensor 1000, with FIG. 1 showing an exploded view of the pressure sensor 1000. The pressure sensor 1000 has an elongate rectangular shape and a rounded end. A geometry of this type provides advantages with regard to ease of manufacture, and of handling for implantation. The pressure sensor 1000 consists substantially of a housing frame 1100, pressure transfer membranes 1201 and 1202, and a pressure transducer such as a MEMS chip 1300. The housing frame 1100 includes an internal volume 1103 bounded by various outer walls 1101a-1101d. The outer wall 1101a has a window 1102, and the opposing outer wall 1101d on the underside of the housing frame 1100 likewise has a window 1102' (not visible in FIG. 1). Within the internal volume 1103 of the housing frame 1100, the MEMS chip 1300 is supported and fastened on a support module 1104. The support module 1104 can include a protrusion 1105, which can be used to stabilize the MEMS chip 1300. A major portion of the perimeter of the support module 1104 is decoupled from the outer wall 1101c via recesses 1106 and 1107 running about the longitudinal sides of the support module 1104, with a connection point 1108 being situated between the two ends of the recesses 1106 and 1107 to provide a connection between the support module 1104 and the housing frame 1100.

FIG. 1a shows the pressure sensor 1000 in finished/assembled form, with the assembled housing 1400 being primarily bounded by the housing frame 1100 and the pressure transfer membranes 1201 and 1202. The window 1102 in the outer wall 1101d, and the opposing window 1102' (not visible in FIG. 1*a*), are covered by the pressure transfer membranes 1201 and 1202 and are preferably fixedly connected with respect to the outer walls 1101*a* and 1101*d*. The pressure transfer membranes 1201 and 1202 thus effectively define part of the outer walls of the housing 1400. The opposing outer walls 1101*a* and 1101*d* are preferably identical, and therefore the underside of the housing 1400 appears essentially identical to the upper side shown in FIG. 1*a*. However, alternative versions of the invention include windows 1102 and 1102' offset from one another, whereby the outer walls 1101*a* and 1101*d* have differently-positioned windows 1102 and 1102'.

FIG. 1*b* shows plan views A, B, C and D of the pressure sensor 1000*a*, and parts thereof. Plan view A in FIG. 1*b* shows the housing frame 1100 without the MEMS pressure chip 1300 and the pressure transfer membranes 1201 and 1202, thereby better depicting the outer housing frame wall 1101*a* and the window 1102 therein; the support module 1104 with protrusion 1105 and connection point 1108; and the recesses 1106 and 1107. Plan view B in FIG. 1*b* shows the housing frame 1100 with the MEMS chip 1300 inserted, and supported on the support module 1104 such that it is decoupled from the housing frame 1100 by the recesses 1106 and 1107 on its opposing longitudinal sides. The protrusion 1105 can be used to stabilize the MEMS chip 1300. Plan view C in FIG. 1*b* shows the housing 1400 of the pressure sensor, in particular its housing frame 1100 with the pressure transfer membranes 1201 and 1202 installed (with membrane 1202, on the underside, not being visible). Plan view D in FIG. 1*b* shows an alternative version of the housing frame similar to housing frame 1100, but omitting the protrusion so that the support module 1501 is planar and directly adjoins the connection point 1502.

Figure 2:
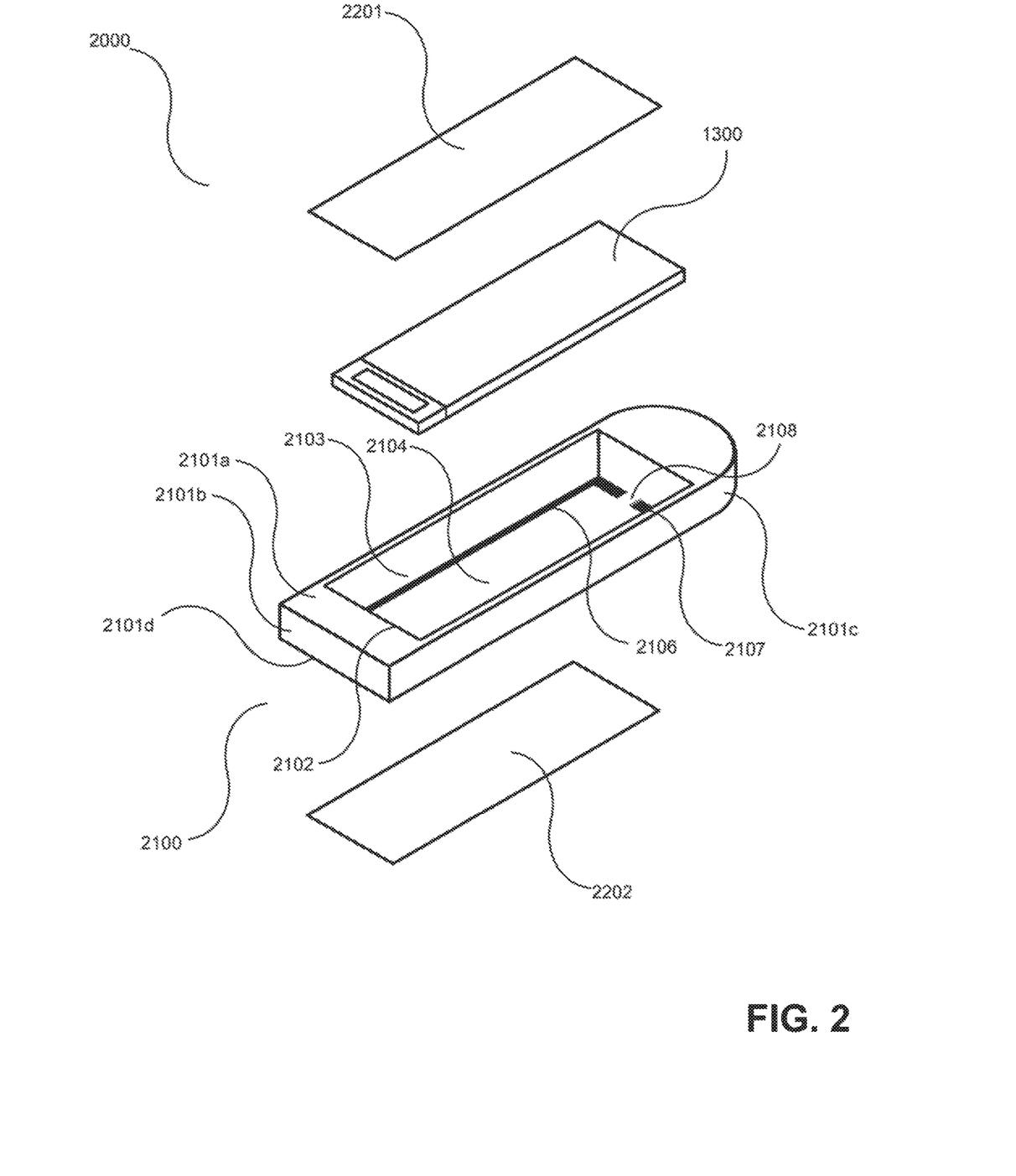
FIG. 2 shows an exploded view of another version of the implantable pressure sensor.
Figure 2A:
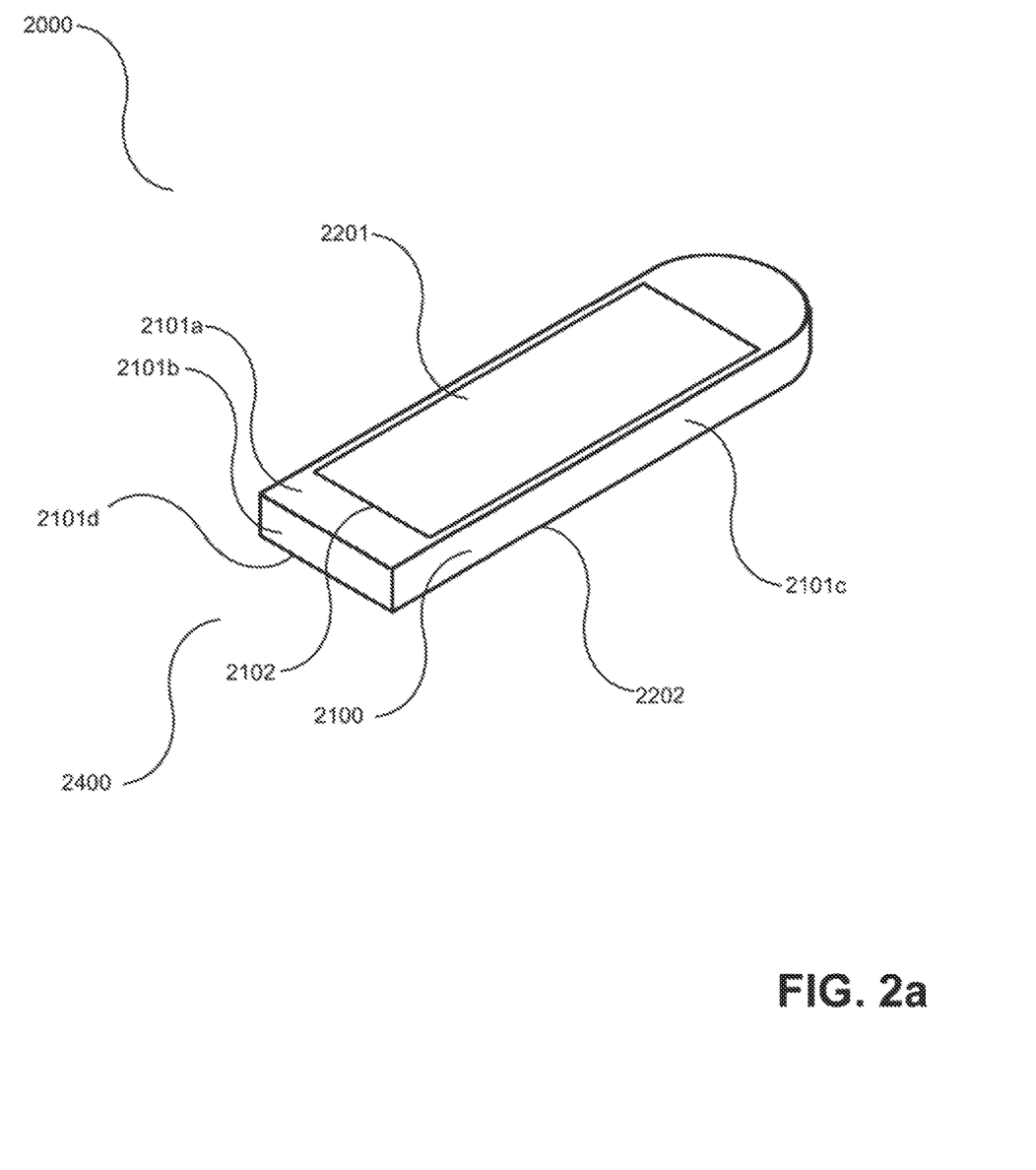
FIG. 2a shows a perspective view of the implantable pressure sensor of FIG. 2 in a finished/assembled form.
Figure 2B:
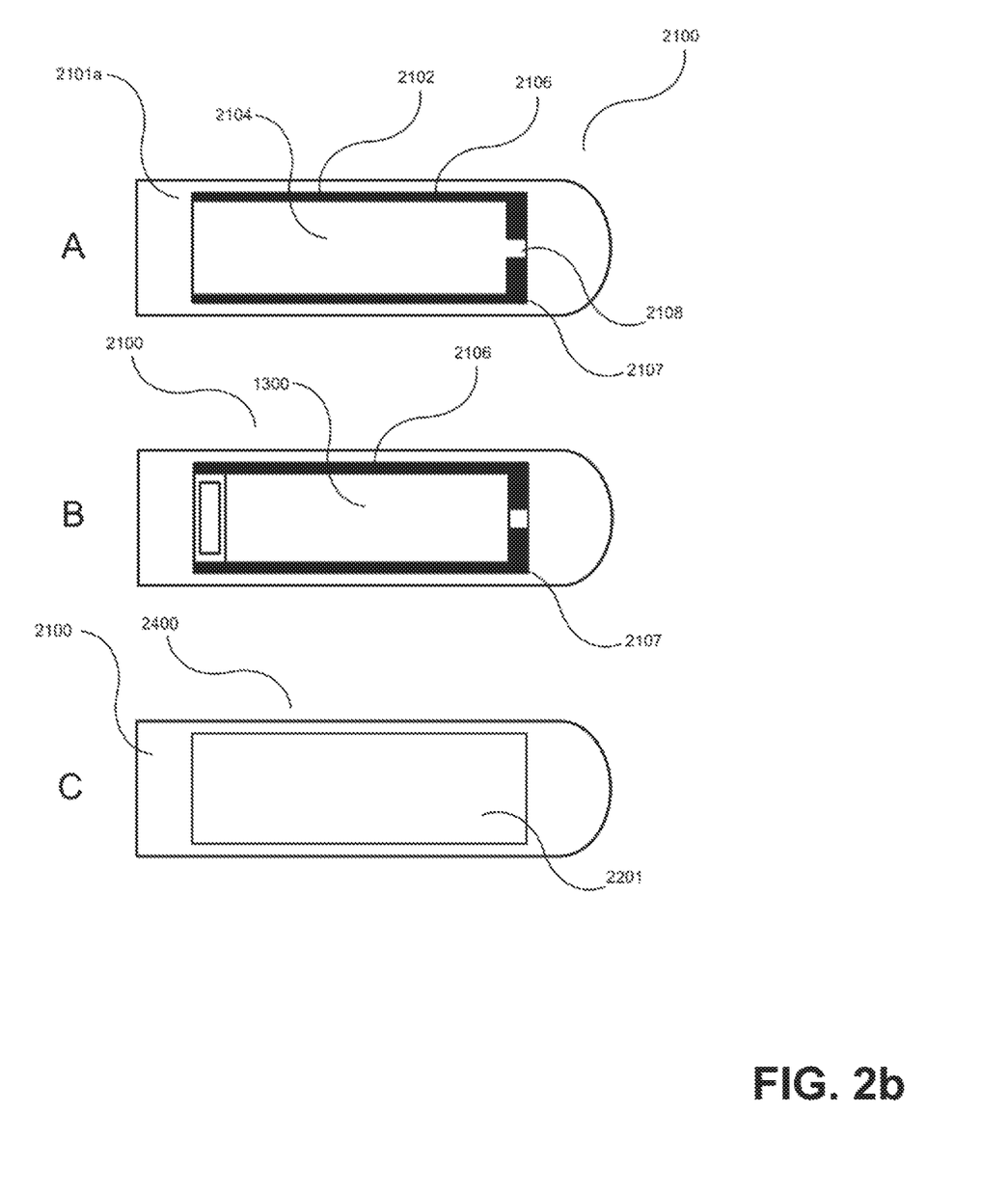
FIG. 2b shows plan views of the implantable pressure sensor of FIG. 2.

FIGS. 2, 2*a* and 2*b* show another exemplary version of the invention in various perspectives, with FIG. 2 showing an exploded view of an implantable pressure sensor 2000. The pressure sensor 2000 has an elongate rectangular shape with a rounded end. Similar to the pressure sensor 1000, the pressure sensor 2000 consists substantially of a housing frame 2100, pressure transfer membranes 2201 and 2202, and a MEMS chip 1300. The housing frame 2100 includes various outer walls 2101*a*-2101*d* about an internal volume 2103, wherein the MEMS chip 1300 is supported and fastened on a support module 2104. The outer wall 2101*a* has a window 2102, and the outer wall 2101*d* on the underside of the housing frame 2100 similarly has a window 2102' (not visible in FIG. 2). Recesses 2106 and 2107 run along the longitudinal sides of the support module 2104 and decouple the support module 2104 from the outer wall 2101*c* at these sides. The connection point 2108 between the opposing ends of the recesses 2106 and 2107 provides a material connection between the support module 2104 and the housing frame 2100. In comparison to the pressure sensor 1000, the internal volume 2013 of the pressure sensor 2000 is cuboidal and does not have a rounded end, unlike the internal volume 1013 of the pressure sensor 1000. The windows 2102 and 2102' formed in the outer walls 2101*a* and 2101*d*, and also the pressure transfer membranes 2201 and 2202, are rectangular and do not have a rounded end, which can reduce manufacturing costs and burdens.

FIG. 2*a* shows the pressure sensor 2000 in the finished/assembled form. The assembled housing 2400 is largely defined by the housing frame 2100 and the pressure transfer membranes 2201 and 2202. The window 2102 in the outer wall 2101*a*, and the window 2102' in the outer wall 2101*d* (not visible in FIG. 2*a*), are covered by the pressure transfer membranes 2201 and 2202. The pressure transfer membranes are preferably fixedly connected to the outer walls 2101*a* and 2101*d* of the housing 2400, and thus form part of the outer walls. The outer walls 2101*a* and 2101*d* are preferably identical and therefore the appearance of the underside of the housing 2400 corresponds to the appearance of the upper side seen in FIG. 2*a*. However, alternative versions of the invention encompass windows 2102 and 2102' are offset from one another, whereby the outer walls 2101*a* and 2101*d* then differ by the position of their windows.

FIG. 2*b* shows plan views A, B and C of the pressure sensor 2000 and parts thereof. Plan view A in FIG. 2*h* shows the housing frame 2100 without the MEMS pressure chip 1300 and pressure transfer membranes 2201 and 2202. The outer wall 2101*a* of the housing frame (with window 2102), the support module 2104 with connection point 2108, and the recesses in the form of recesses 2106 and 2107 can be seen. Plan view B in FIG. 2*b* shows the housing frame 2100 with the MEMS chip 1300 inserted. The MEMS chip 1300 is supported on the support module 2104 such that it is decoupled from the housing frame 2100 by the recesses 2106 and 2107 on its opposing longitudinal sides. Plan view C in FIG. 2*b* shows the housing 2400, and its housing frame 2100 and pressure transfer membranes 2201 (and 2202 on the underside).

Figure 3A:
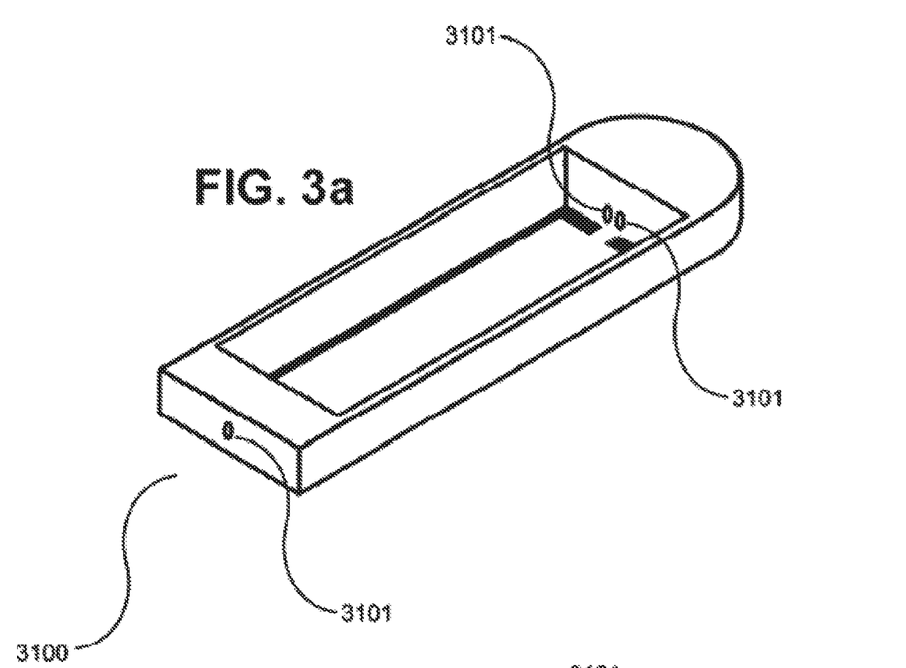
FIGS. 3a and 3b show an alternative pressure sensor housing having apertures.
Figure 3B:
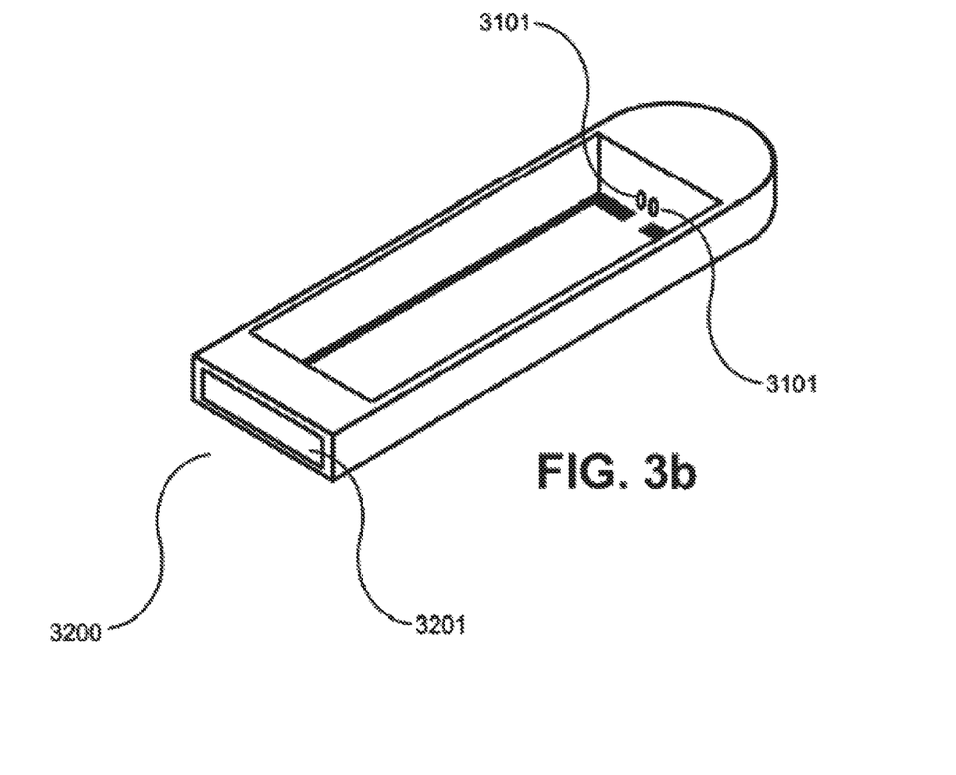

FIGS. 3*a* and 3*b* show alternative versions of the invention with apertures in the depicted housing frames 3100 and 3200, which are otherwise configured similarly to the housing frame 2100 of FIG. 2. However, such apertures can be provided in housing frames having other configurations, or at different locations on the housing. The housing frame 3100 has apertures in the form of small holes 3101 at its ends, whereas the housing frame 3200 has an aperture of rectangular shape 3201 at one of its ends. The apertures can be used, for example, to connect a MEMS chip located inside the housing to other electrical components, and/or to fill the internal volume of the housing with the pressure transfer medium (for example oil) after the housing has been assembled. The apertures are preferably formed such that they can be closed.

Figure 4:
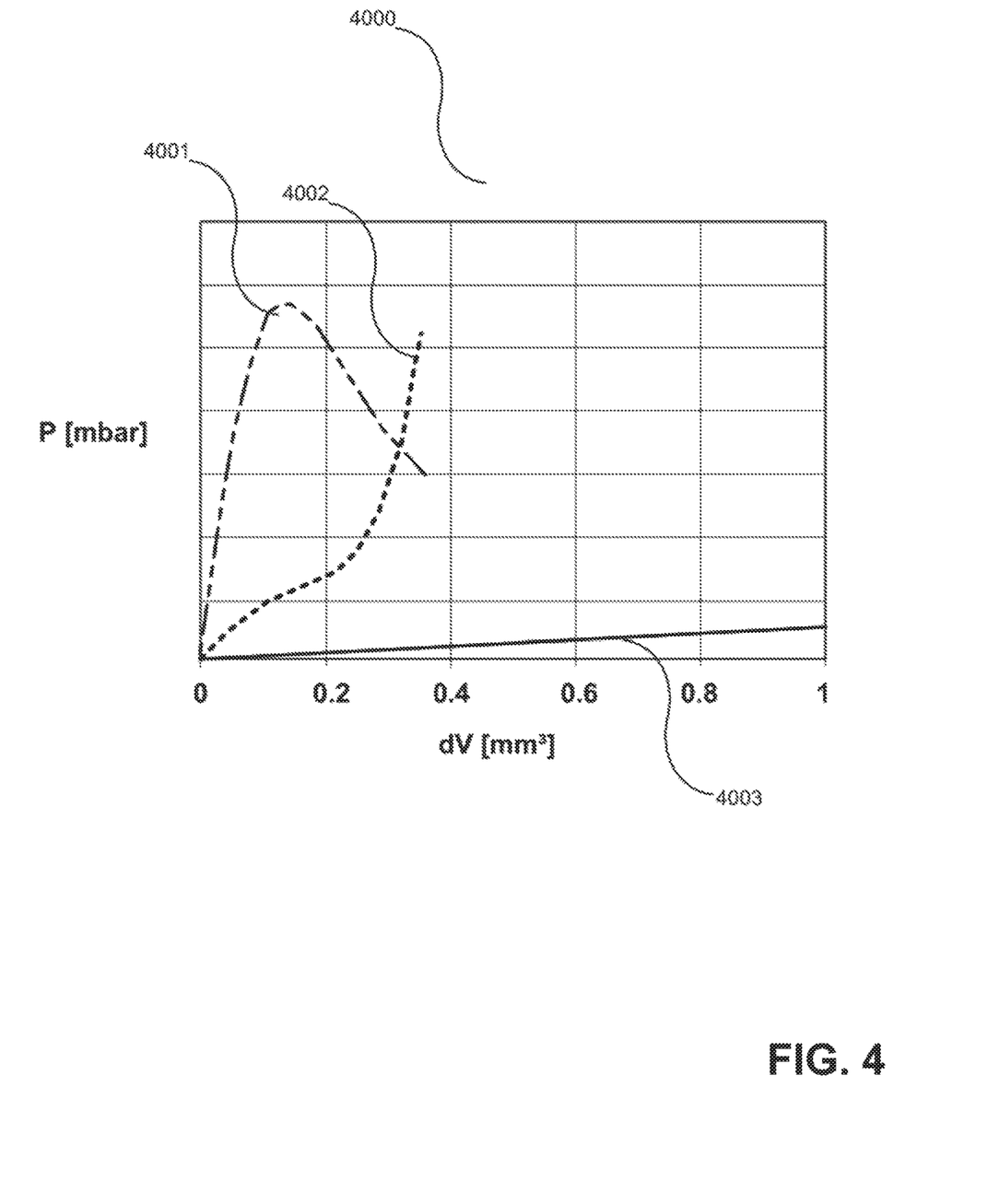
FIG. 4 show pressure-volume curves exemplifying prior art housings and housings in accordance with the present invention.

FIG. 4 shows a pressure-volume graph 4000 having pressure-volume curves of pressure sensors having different housings. Curves 4001 and 4002 illustrate pressure conditions P depending on a change in volume $\Delta V$ inside the housing for known housings wherein a pressure transfer membrane is mounted on one side of the housing. The curve 4003 represents the pressure-volume behavior of an exemplary pressure sensor according to the invention. In the curves 4001 and 4002 of the known housings, the pressure P changes sharply and in a non-linear manner for even just small changes in volume $\Delta V$, whereas the pressure P for the housing according to the invention rises at least substantially linearly and only moderately, even in the event of large volume changes $\Delta V$.

Figure 5:
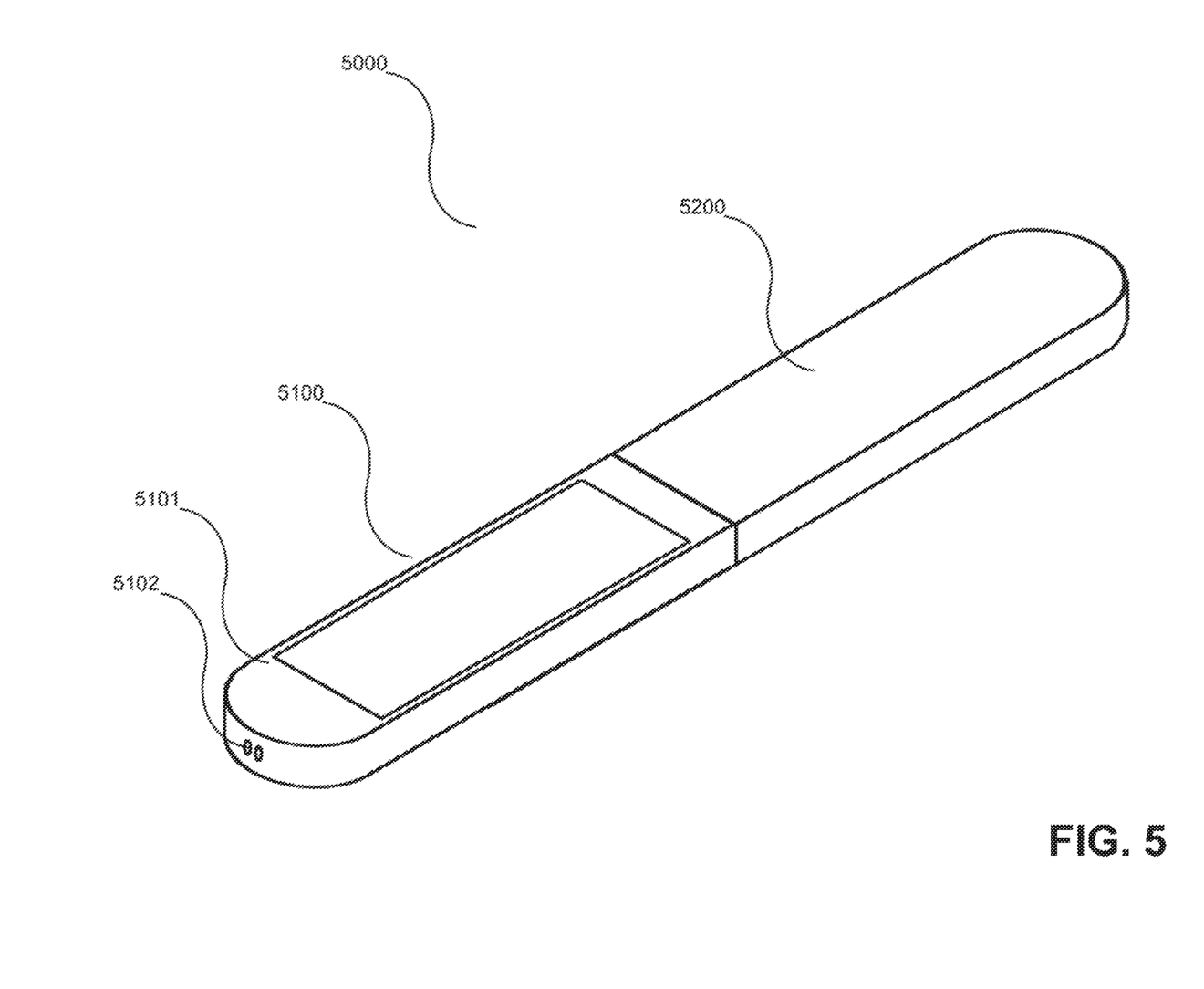
FIG. 5 shows an exemplary version of the implantable pressure sensor with a connected battery module.

FIG. 5 schematically illustrates a structure 5000 consisting of a version of the implantable pressure sensor 5100 according to the invention in combination with a module 5200, which could be (for example) a battery, a memory or other data storage unit, a microprocessor, a wireless data transceiver, or some combination of these components. The pressure sensor 5100 has a housing 5101, which may optionally include apertures 5102 on its end faces. The module 5200 is fixedly connected to the pressure sensor 5100 at a flat end face of both components. Both the pressure sensor 5100 and the module 5200 have a rounded end, such that the structure 5000 presents fewer corners, which provides advantages for the implantation process and biocompatibility. The pressure sensor 5100 and module 5200 can be electrically connected, for example, via an aperture at the contact points of both components.

Figure 6A:
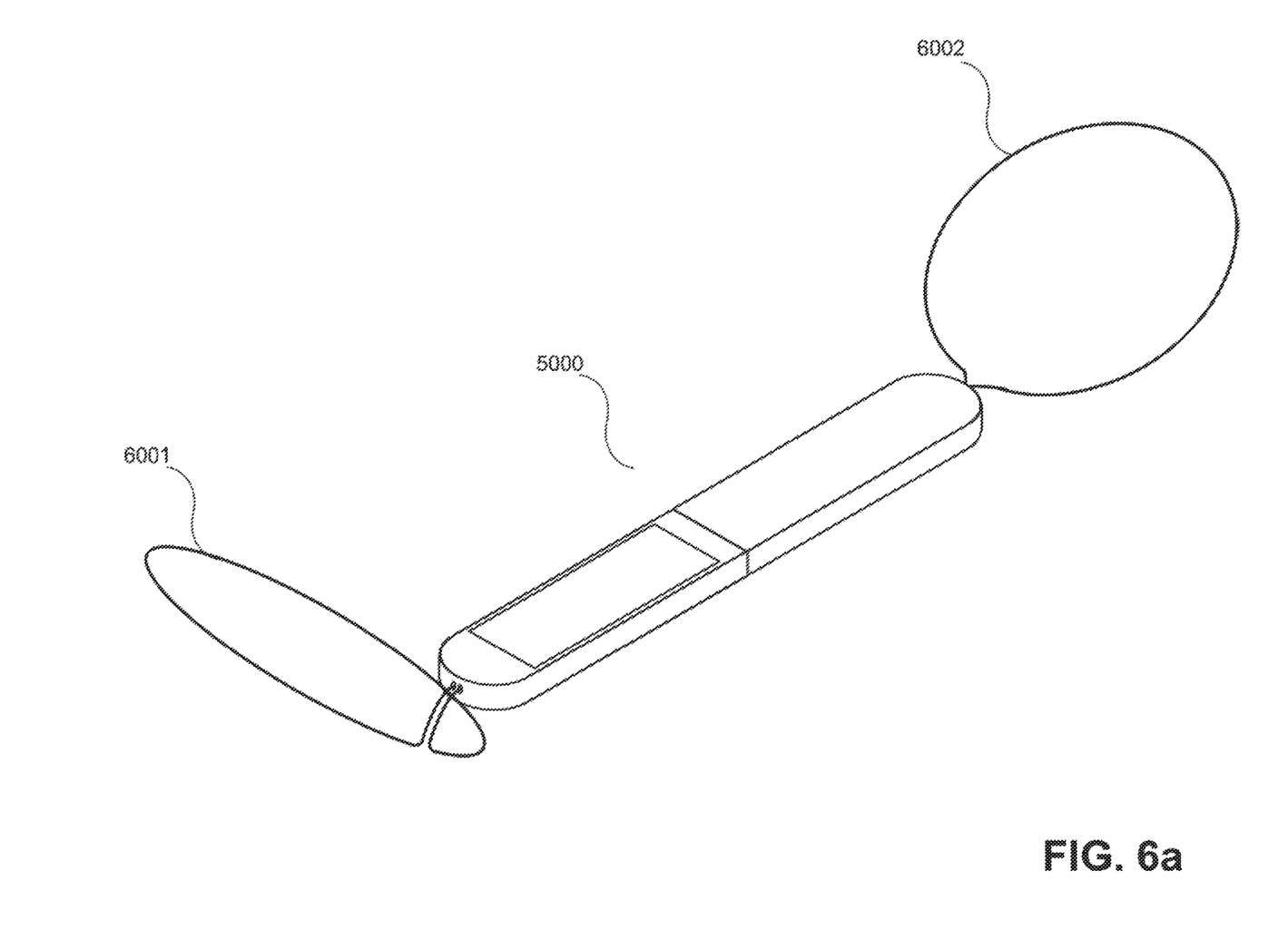
FIGS. 6a and 6b show exemplary versions of the implantable pressure sensor with connected battery modules and fastening devices.
Figure 6B:
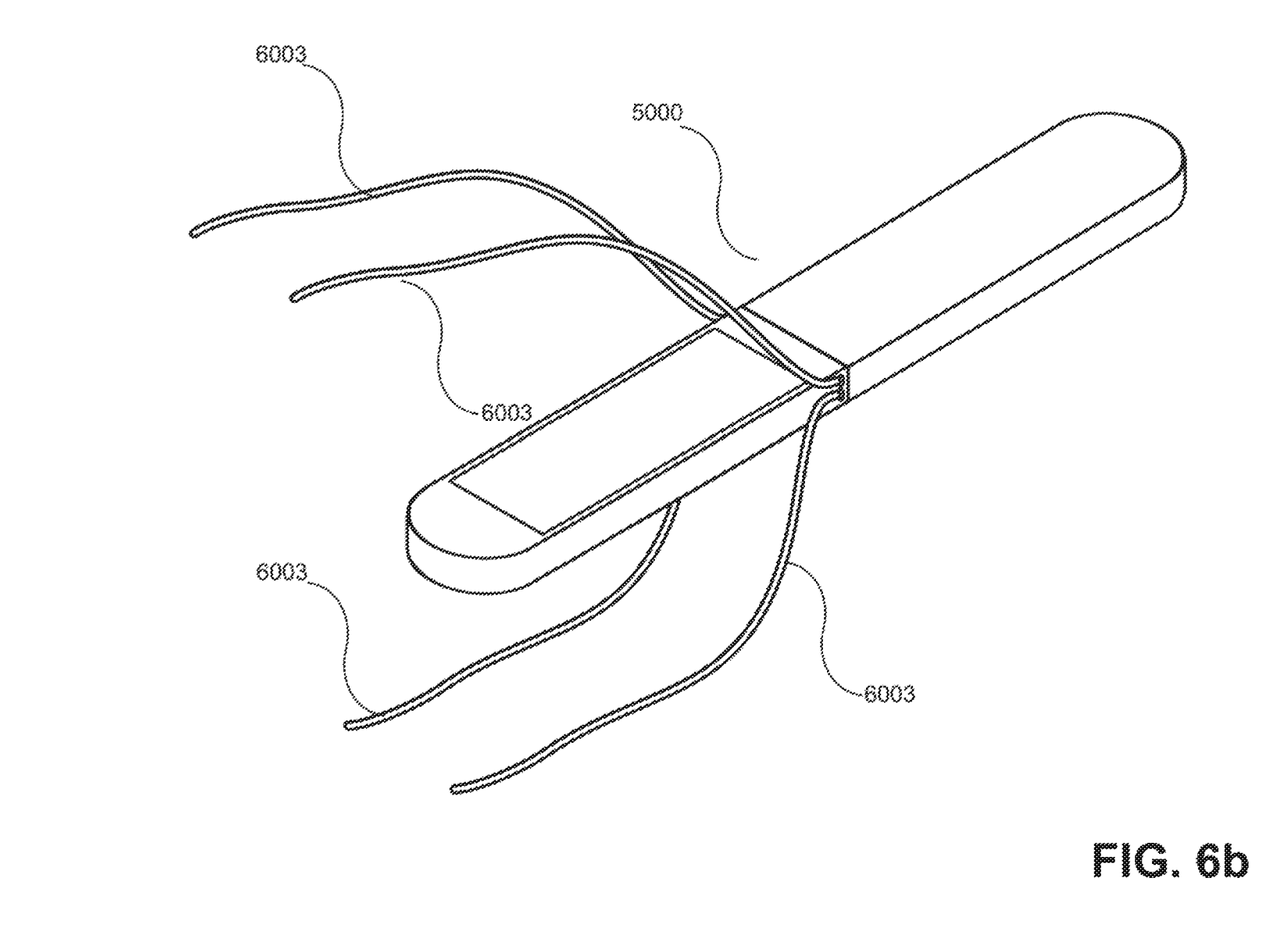

FIGS. 6a and 6b schematically illustrate the structure 5000 of FIG. 5, with additional components for stabilizing or anchoring the structure at an implantation site. FIG. 6a shows the structure 5000 with wire loops 6001 and 6002 fastened to the end faces. The wire loops can hold the structure 5000 at an implantation site within a vessel, for example in the pulmonary artery, which has a greater diameter than the structure 5000 itself. At the same time, bodily fluids (such as blood) can continue to flow through the vessel. Wire loops 6001 and/or 6002 can optionally be used as antennas for wireless communication between the pressure sensor and an external unit. Wire loops 6001 and 6002 can advantageously be in a folded state prior to and during the implantation process, thereby facilitating conveyance to the implantation site, and can be brought into an unfolded state at the implantation site. The structure 5000 can also be held at the implantation site an arrangement such as that shown in FIG. 6b. Here wire arms 6003 are fastened to the structure 5000 (e.g., at openings formed on the housing of the pressure sensor), and likewise ensure that the implant is fastened at an implantation site having a diameter larger than the structure 5000 itself. The wire arms 6003 are preferably resilient.

While the accompanying drawings depict planar pressure transfer membranes (when unstressed), the unstressed pressure transfer membranes need not be planar, and could (for example) have a curved/domed or wavy profile, at least along an outer or inner surface thereof. An exemplary preferred pressure transfer membrane has an undulating inner face, which can exhibit improved bending properties.

While the housings discussed above are well suited for use in pressure sensor applications, the principles described herein can be used in other applications wherein it is useful to compensate for volume changes to enhance functionality of electronic components, for example, where volume changes are caused by chemical processes in Li-ion batteries.

The dimensions and other values specified above are merely exemplary, and can be different in other versions of the invention. The invention is not intended to be limited to the exemplary versions of the invention discussed above, but rather is intended to be limited only by the claims set out below. Thus, the invention encompasses all different versions that fall literally or equivalently within the scope of these claims.

The invention claimed is:

1. An implantable pressure sensor housing including:
   a. housing walls bounding an internal volume,
   b. a support module within the internal volume, the support module extending from the housing walls,
   c. recesses extending between the support module and the housing walls on opposite sides of the support module, the recesses having recess ends extending inwardly toward each other whereby a narrowed region is defined on the support module between the recess ends, the narrowed region being joined to the housing walls,
   d. a pressure transducer situated within the internal volume, and
   e. two or more pressure transfer membranes, wherein the pressure transfer membranes are:
      (1) discontinuous, and
      (2) situated in different planes.

2. The housing of claim 1 wherein:
   a. the housing walls include two or more discrete walls, and
   b. two or more of the discrete walls each bear one of the pressure transfer membranes thereon.

3. The housing of claim 2 wherein the two discrete walls are opposite each other.

4. The housing of claim 2 wherein the recesses extend between the pressure transfer membranes.

5. The housing of claim 1 wherein at least one of the housing walls is at least partially flexibly and reversibly deformable.

6. The housing of claim 1 wherein each recess is situated adjacent the internal volume of the housing.

7. The housing of claim 1 wherein each recess is defined by an aperture or depression situated adjacent an inner surface of one of the housing walls.

8. The housing of claim 1 wherein at least one of the pressure transfer membranes borders the recess.

9. The housing of claim 1 wherein the support module extends from one or more of the housing walls.

10. The housing of claim 9 wherein the support module is bounded on opposing sides by a recess, with the support module being connected to the housing walls at connection points between the opposing sides.

11. The housing of claim 1 further including a fluid pressure transfer medium filling the internal volume of the housing.

12. The housing of claim 11 wherein the fluid pressure transfer medium is a liquid.

13. The housing of claim 1 further including an aperture defined in the housing walls between the internal volume of the housing and the exterior of the housing.

14. The housing of claim 1 wherein the pressure transducer is spaced from the housing walls and the pressure transfer membranes by the recesses, whereby the pressure transducer is isolated from flexure in the housing walls and/or the pressure transfer membranes.

15. The housing of claim 1 wherein the recesses surround a major portion of a perimeter of the support module.

16. The housing of claim 1 wherein:
   a. the support module and the pressure transducer are situated within a depression extending into a first side of the housing, and
   b. one of the pressure transfer membranes is situated:
      (1) over the depression, and
      (2) spaced from the pressure transducer.

17. An implantable pressure sensor housing including:
   a. an internal volume bounded by:
      (1) housing walls, and
      (2) two or more pressure transfer membranes, each pressure transfer membrane being:
         i. bounded by one or more of the housing walls,
         ii. discrete and separate from each other pressure transfer membrane, and
         iii. situated in a different plane than at least one of the other pressure transfer membranes,
   b. a support module:
      (1) extending into the internal volume from the housing walls,
      (2) spaced from the pressure transfer membranes, and
      (3) having opposing sides spaced from the housing walls by recesses, the recesses having recess ends extending inwardly toward each other whereby a narrowed region is defined on the support module between the recess ends, the narrowed region being joined to the housing walls, c. a pressure transducer situated within the internal volume, wherein the pressure transducer is spaced from the housing walls and from the pressure transfer membranes, whereby the pressure transducer is isolated from flexure in the housing walls and/or the pressure transfer membranes.

18. An implantable pressure sensor housing including:
a. housing walls partially bounding an internal volume,
b. pressure transfer membranes, each pressure transfer membrane:
   (1) also partially bounding the internal volume,
   (2) being situated within the housing walls, and
   (3) being spaced from the other pressure transfer membranes,
c. a support module extending from the housing walls,
d. recesses situated on opposite sides of the support module between the support module and the housing walls, the recesses having recess ends extending inwardly toward each other whereby a narrowed region is defined on the support module between the recess ends, the narrowed region being joined to the housing walls,
e. a pressure transducer within the internal volume, wherein the pressure transducer is situated between and spaced from:
   (1) the housing walls, and
   (2) the pressure transfer membranes,
   whereby the pressure transducer is isolated from flexure in the housing walls and/or the pressure transfer membranes.

19. The implantable pressure sensor housing of claim 18 wherein each pressure transfer membrane is situated in a different plane than at least one of the other pressure transfer membranes.

* * * * *